Figure 1:
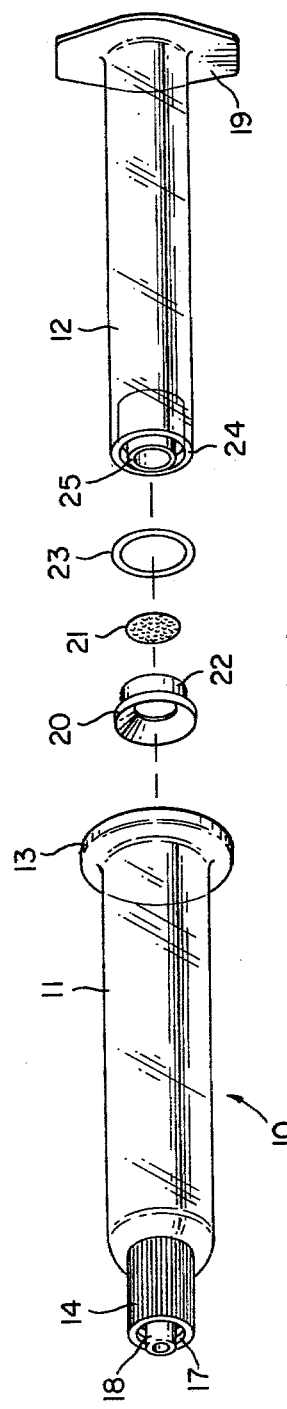

United States Patent [19]

Ford, Jr.

[11] 4,327,745
[45] May 4, 1982

[54] BLOOD SAMPLING DEVICE

[75] Inventor: George W. Ford, Jr., Sandy, Utah

[73] Assignee: The Deseret Company, Sandy, Utah

[21] Appl. No.: 182,874

[22] Filed: Sep. 2, 1980

[51] Int. Cl.³ .............................................. A61B 5/00
[52] U.S. Cl. ................................................. 128/765
[58] Field of Search .............. 128/766, 765, 763, 767, 128/760; 424/101

[56] References Cited

U.S. PATENT DOCUMENTS

| 3,660,037 | 5/1972 | Sokol | 128/765 |
| 3,802,843 | 4/1974 | Kim | 422/101 |
| 3,960,139 | 6/1976 | Bailey | 128/765 X |
| 3,978,846 | 9/1976 | Bailey | 126/765 X |
| 4,099,520 | 7/1978 | Decker et al. | 128/760 |
| 4,212,309 | 7/1980 | Moorehead | 128/765 |

*Primary Examiner*—John D. Yasko
*Attorney, Agent, or Firm*—Albert H. Graddis

[57] ABSTRACT

An arterial blood sampling syringe consisting of a barrel and a plunger assembly in which the plunger is hollow and provided at its distal end with two annular rings which cooperate with the hollow plunger and each other to maintain a sealing ring and gas-pervious but liquid impervious membrane in position at the end of the plunger. The plunger position in the barrel may be preset to receive any desired blood sample volume. Further blood flow is halted when the barrel of the syringe fills to the volume desired.

1 Claim, 2 Drawing Figures

U.S. Patent   May 4, 1982   4,327,745

BLOOD SAMPLING DEVICE

The present invention relates to a unique sampling device suitable for obtaining arterial blood samples for blood gas analysis.

Measurements of the blood level of carbon dioxide ($PCO_2$) and of oxygen ($PO_2$) as well as blood pH constitute a quick reliable diagnostic regimen for determination of respiratory parameters and acid-base balance. However, since arterial blood rather than venous blood, which is used in most clinical laboratory procedures, must be obtained for such blood gas analysis and the fact that the gases being analyzed for are extremely sensitive to influences from the outside environment, special devices must be used to preserve the integrity of the specimen.

A device which is used for sampling arterial blood should function in the following manner: The device should be constructed to fill under arterial blood pressure but should be resistant enough to prevent the lower venous pressures from filling the device. This function allows for discrimination of the specimen being obtained. The device should present a barrier to the outside environment which will prevent gas exchange with the ambient atmosphere. The device should have some means of removing trapped gas within the device which again would allow for gas exchange.

Finally, the device must have fitment means by which a hollow hypodermic needle may be attached to collect the sample. This fitment should be of proper caliber and configuration to allow interface with instrumentation used in blood gas analysis and other purposes.

IN THE DRAWING

Figure 2:
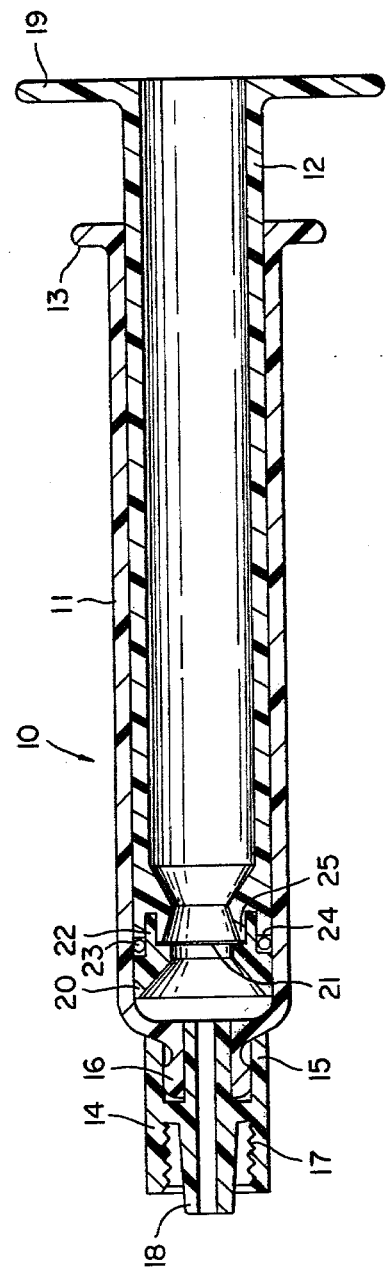

FIG. 1 is an exploded view in perspective of the blood sampling device of this invention showing the manner in which the several parts are assembled, and FIG. 2 is a cross sectional view of the blood sampling device with the several parts in position prior to drawing an arterial blood sample. Like numerals indicate like parts throughout the several views of the drawing.

Referring now to both FIG. 1 and FIG. 2 of the drawing, the blood sampling device of this invention, generally indicated by reference numeral 10, comprises a barrel 11 and plunger assembly whose primary component is a hollow piston 12. Barrel 11 is provided at one end with a circumferential annular lip 13 and at the other end with a fitting 14. Barrel 11 may be formed out of glass or of a clear molded plastic material whose composition is such as to present a barrier to atmospheric gas. When barrel 11 is molded, the element forming fitting 14 may be molded integrally with the barrel. In the embodiment shown, fitting 14 comprises a separate element, as can be seen in FIG. 2. To assemble the parts, fitting 14 is mounted on barrel 11 by means of a sleeve or collar portion 15 which fits over a hub 16 molded as a part of the distal end of barrel 11 with a suitable adhesive being employed to join the parts or by providing dimensions for a force or friction fit. The interior of fitting 14 is provided with threads 17 which are shaped to accept a removable hollow hypodermic needle (not shown) whose external hub is provided with complementary lugs which allow for a locking screw assembly or whose inner bore can be mounted by force fit over the outer surface of projecting stem 18.

The plunger assembly which in normal operating position fits into the interior of barrel 11, as shown in FIG. 2, comprises in addition to hollow piston 12 whose proximal end is shaped to provide a handle 19, a membrane and sealing ring assembly mounted on the distal end of piston 12 whose several elements are more particularly shown in exploded view in FIG. 1. The membrane and sealing ring assembly comprises an annular ring 20, the interior of which is provided with a membrane medium in the form of a disk 21 and on whose flange 22 is seated an O-ring 23. When the several parts are brought together in assembled position, as shown in FIG. 2, the O-ring 23 is held in seated position between annular ring 20 and the end surface 24 of piston 12, with the inner surfaces of flange 22 of annular ring 20 fitting over circular lip 25 molded into and forming the end of piston 12.

Thus, when the parts are assembled, the membrane disk 21 is held firmly in position within annular ring 20 by the pressure exerted by circular lip 25 against disk 21 when annular ring 20 and flange 22 are placed over circular lip 25 and firmly seated in position. With the parts as assembled, O-ring 23 also acts as a seal between the inner surface of barrel 11 and the outer surface of piston 12. The structure of membrane disk 21 allows for free passage of gases but this material is structured such that when a liquid such as blood, for example, wets the surface an ionic equilibrium between the surface tension of the liquid and the equilibrium between the membrane is reached and no fluid will pass through the membrane. Suitable materials for this purpose are those known in the art as hydrophobic membrane. Furthermore, when the membrane is in ionic equilibrium with the liquid contained inside the barrel 11, the only means by which gas may now exchange is by Brownian motion across a high resistance. Driving pressures which would allow for such exchange do not exist in the environment in barrel 11.

Before final assembly of piston 12 into barrel 11, crystalline heparin may be introduced into barrel 11. The presence of heparin acts as an anticoagulant to prevent the blood specimen from clotting which would destroy its integrity for accurate blood gas analysis. As the anticoagulant is in crystalline form, no dilution of the specimen obtained takes place as is the case with heparin in solution. After adding the anticoagulant the plunger assembly 12 is inserted into the barrel assembly 11.

When drawing an arterial blood sample using blood sampling device of this invention, barrel 11 is held firmly in one hand and handle 19 is used to retract piston 12 to a position where the volume of open space in barrel 11 is equivalent to the volume of the blood sample to be drawn. A hollow hypodermic needle of the usual type (not shown) is then locked under the threads 17 or placed firmly over stem 18 and the beveled end of the needle then introduced into an available artery such as the radial or brachial artery. On penetration of the arterial wall, the internal arterial blood pressure will force blood to flow through the needle and into the blood sampling device. Since the structure of the membrane disk 21 permits gas to flow through it, as the blood sampling device fills with arterial blood the gas present in barrel 11 will be displaced through disk 21 and will leave barrel 11 through the interior of hollow piston 12. When the blood level reaches disk 21, an ionic equilibrium between the surface tension of the liquid and the ionic charge of the membrane is reached and a seal is formed preventing the passage of the blood through the membrane. The needle is then withdrawn from the artery and the blood sampling device is rotated to dissolve the crystalline anticoagulant into the sample to prevent clotting. Pressure is applied to the arterial wall to allow the normal blood coagulation process to close off the narrow puncture wound. The chamber of the blood sampling device is now sealed by membrane disk 21, and the blood sample may be introduced directly into instrumentation which is facilitated by the particular caliber and configuration of fitting 14.

I claim:

1. A syringe device for drawing an arterial blood sample including a hollow barrel open at one end and having a hypodermic needle removably mounted at the other end, a plunger assembly within the open end of said barrel for slidable reciprocating movement therein, said plunger assembly including a hollow piston with a first annular fitting within said hollow piston having an external diameter smaller than said hollow piston and of a dimension to allow it to be fixedly mounted within the distal end of said hollow piston, an integral skirt of a lesser diameter dependent therefrom, a second annular fitting comprising a cylindrical upper section having an internal diameter to cooperate with and receive said dependent integral skirt for a force fit therebetween and of an external diameter to form a force fit within said hollow piston, said second annular fitting also including an inner shoulder and an outer shoulder, said outer shoulder being adapted to receive a sealing ring for sealing the space between the hollow barrel and piston when said hollow barrel and second annular fitting are assembled, said internal shoulder cooperating with the dependent skirt of said first annular fitting for supporting and fixedly maintaining a membrane element therebetween, said membrane element being pervious to the passage of air therethrough but impervious to the passage of liquid after being wetted.

* * * * *